US006822183B2

(12) United States Patent
Walker

(10) Patent No.: US 6,822,183 B2
(45) Date of Patent: Nov. 23, 2004

(54) METHOD OF SELECTING WOOD FOR CHEMICAL PULPING

(75) Inventor: John Corrie Fleming Walker, Christchurch (NZ)

(73) Assignee: Canterprise Limited (NZ)

(*) Notice: Subject to any disclaimer, the term of this patent is extended or adjusted under 35 U.S.C. 154(b) by 114 days.

(21) Appl. No.: 10/074,723

(22) Filed: Feb. 12, 2002

(65) Prior Publication Data

US 2002/0112542 A1 Aug. 22, 2002

(30) Foreign Application Priority Data

Feb. 13, 2001 (NZ) .............................. 509847

(51) Int. Cl.⁷ .............................................. B07C 5/00
(52) U.S. Cl. ........................................ 209/590; 73/597
(58) Field of Search .......................... 209/576, 590, 209/517, 518; 162/49, 55; 73/587, 597

(56) References Cited

U.S. PATENT DOCUMENTS

| | | | | |
|---|---|---|---|---|
| 4,794,545 A | * | 12/1988 | Salvado | 702/30 |
| 4,837,446 A | * | 6/1989 | Renard et al. | 250/461.1 |
| 5,013,403 A | * | 5/1991 | Chase | 162/49 |
| 5,282,931 A | * | 2/1994 | LeClerc et al. | 162/49 |
| 6,256,600 B1 | * | 7/2001 | Bolton et al. | 703/6 |
| 2001/0017195 A1 | * | 8/2001 | Trung et al. | 162/49 |

FOREIGN PATENT DOCUMENTS

WO WO 91/10904 * 7/1991

* cited by examiner

Primary Examiner—Donald P. Walsh
Assistant Examiner—Joseph C Rodriguez
(74) Attorney, Agent, or Firm—McCormick, Paulding & Huber LLP; Chester E. Flavin

(57) ABSTRACT

A method of selecting bulk wood units for chemical pulping in alkaline conditions which consists of establishing a reference scale by selecting a test sample, measuring the acoustic velocity through each sample units, selecting acoustic velocity bands from the sample results, processing the sample units using known chemical pulping processes, measuring the percentage pulp yield, and then using the measured pulp yields and acoustic velocities to produce a reference scale; measuring the acoustic velocity through each of the units, comparing the velocity measurement for each unit against the reference scale, and then dividing the tested units into subgroups according to the predicted yield in chemical pulping.

6 Claims, 5 Drawing Sheets

METHOD OF SELECTING WOOD FOR CHEMICAL PULPING

TECHNICAL FIELD

The present invention relates to a method of selecting bulk wood units for chemical pulping under alkaline conditions. As used herein, the term "bulk wood units" refers to logs or log segments or large planks of wood; the method of the present invention is designed predominantly for use in selecting or classifying unsawn logs, but it could also be used for selecting or classifying log segments or large sawn planks. As used herein, the term "chemical pulping" includes semi-chemical pulping, i.e. processes in which wood is chemically pre-treated in a manner similar to chemical pulping, and then mechanically pulped.

BACKGROUND ART

The chemical pulping of wood to produce pulp for papermaking may be carried out by a number of different known techniques: the present invention relates specifically to those techniques which involve digesting the chipped wood in a bath of digester fluid which is alkaline based. The digester process generally is carried out at an elevated temperature and pressure.

The object of all of the digestion processes is to dissolve the lignin in the wood to release the individual fibres, leaving the cellulose and alkali-resistant hemicelluloses in the fibre walls. A typical wood sample has about 30 percent lignin, and this is reduced during the digestion processes to about 5%; the remaining 5% is removed from the pulp by bleaching. The lignin in the wood glues the fibres together and infiltrates between the cellulose and other constituents of the wood. It follows that the higher the percentage of cellulose and alkali-resistant hemicelluloses in the wood, the less lignin there is to be dissolved during the digestion stages, and the less bleaching is required; thus, the lower the percentage of lignin, (or the higher the percentage of cellulose) the lower the process costs. Hereinafter, the term 'cellulose' is taken to include both cellulose and residual alkali-resistant hemicellulose.

The most commonly used chemical pulping process is the sulphate or Kraft process, in which the wood chips are cooked in a mixture of caustic soda and sodium sulphide. The method of the present invention has been developed with the special reference to the Kraft process and therefore will be described with particular reference to this process. However, it will be appreciated that the method of the present invention also may be applied to select wood for any of the alkaline-based chemical or semi chemical pulping processes, (i.e. where the pH >7).

It is well established in the industry that some wood has a higher cellulose content, and therefore would be more efficient to process by chemical pulping. However, identifying which wood has a higher cellulose content simply cannot be achieved using current log sorting methods.

The traditional method of sorting trees at the point of harvest of the log is to categories and grade logs according to their diameter, length, straightness, diameter eccentricity and visual defects; the logs are placed in categories which reflect log diameter, log size and log grade. The basic assumption is that logs in each category are substantially identical. However, so far as chemical pulping yield is concerned, logs sorted in the above manner often prove to be far from identical, and may vary widely in cellulose content.

When a batch of logs is being processed by chemical pulping, it is of considerable economic advantage if all the logs have a similar cellulose content, since this will directly affect processing time and the quantities of processing chemicals required.

There is known to be a relationship between acoustic velocity through a bulk wood unit and its stiffness or modulus of elasticity. U.S. Pat. No. 6,026,689 discloses a system for predicting the modulus of elasticity of a bulk wood unit by generating a stress wave along the length of the unit by striking the unit (e.g. with a hammer), picking up vibrational signals from a standing stress wave in this unit, and using this information to calculate the speed of the stress wave in the unit, and hence the predicted modulus of elasticity for that unit.

It also is known that there is a relationship between the modulus of elasticity of a bulk wood unit and the microfibril angle, i.e. the angle of inclination of the stiff bundles of cellulose chains (microfibrils) which are embedded within the cell walls of the wood tissue. Generally, the microfibril angle is taken to refer to the helical inclination of the cellulose in the S 2 layer of the cell wall. (Page, D H, El-Hosseiny F, Winkler K and Lancaster A F 1877 'Elastic Modules of Single Pulp Fibres' Tappi 60 (4) V 1–4 and Cave I.D. 1988 'The Anisotropic Elasticity of the Plant Cell Wall' Wood Sciences & Technology 2 (4) 168–78).

In the paper by R. H. Newman (University of Canterbury Wood Technology Workshop of 1996), there was shown to be an empirical correlation between the modulus of elasticity of wood and its 'pure' cellulose content (i.e. excludes hemicellulose), but the two properties were not shown to be derived from or directly dependent upon each other. In the development of the method of the present invention, it was postulated that there may be a direct relationship between the microfibril angle and the cellulose content of wood, although such a direct relationship has not yet been proved.

SCOPE OF THE INVENTION

An object of the present invention is the provision is the provision of a method whereby a batch of logs may be reliably and accurately graded according to their likely yield during chemical pulping under alkaline conditions, by utilising the assumption that there is a sufficient relationship between the microfibril angle of wood and the cellulose content of that wood to permit cellulose content (and hence pulping yield) to be predicted from a measurement of acoustic velocity through the wood.

The present invention provides a method for sorting a batch of bulk wood units for chemical pulping under alkaline conditions comprising the steps of:

1) establishing a reference scale for the timber group to be sorted by:
  a) selecting at random a plurality of sample units of bulk wood from the timber group;
  b) measuring the acoustic velocity through each of said sample units using a predetermined measuring technique;
  c) recording said acoustic velocities and grouping said velocities into two or more velocity bands;
  d) processing all or part of each of said sample units to pulp using a predetermined chemical pulping process;
  e) determining the pulp yield from each sample;
  f) producing a reference scale indicating predicted pulp yield for a range of acoustic velocities;

2) measuring the acoustic velocity through each of said bulk wood units in turn, using said predetermined measuring technique;
3) comparing said acoustic velocity measurements against the reference scale to predict the chemical pulping yield for each tested unit; and
4) dividing the tested units into subgroups according to the predicted chemical pulping yield.

Preferably, before said acoustic velocity bands are selected, the acoustic velocities from all of said sample units are graphed to show the distribution of acoustic velocity in the total sample, to enable velocity bands to be selected such that a predetermined proportion of bulk wood units fall within each of the selected velocity bands.

Preferably, each of the batch of bulk wood units would be of the same or a similar species and would have a similar history i.e. each of the bulk wood units would be of a similar age, have been grown under similar conditions, and managed in a similar fashion.

DETAILED DESCRIPTION OF THE PREFERRED EMBODIMENT

Figure 1:
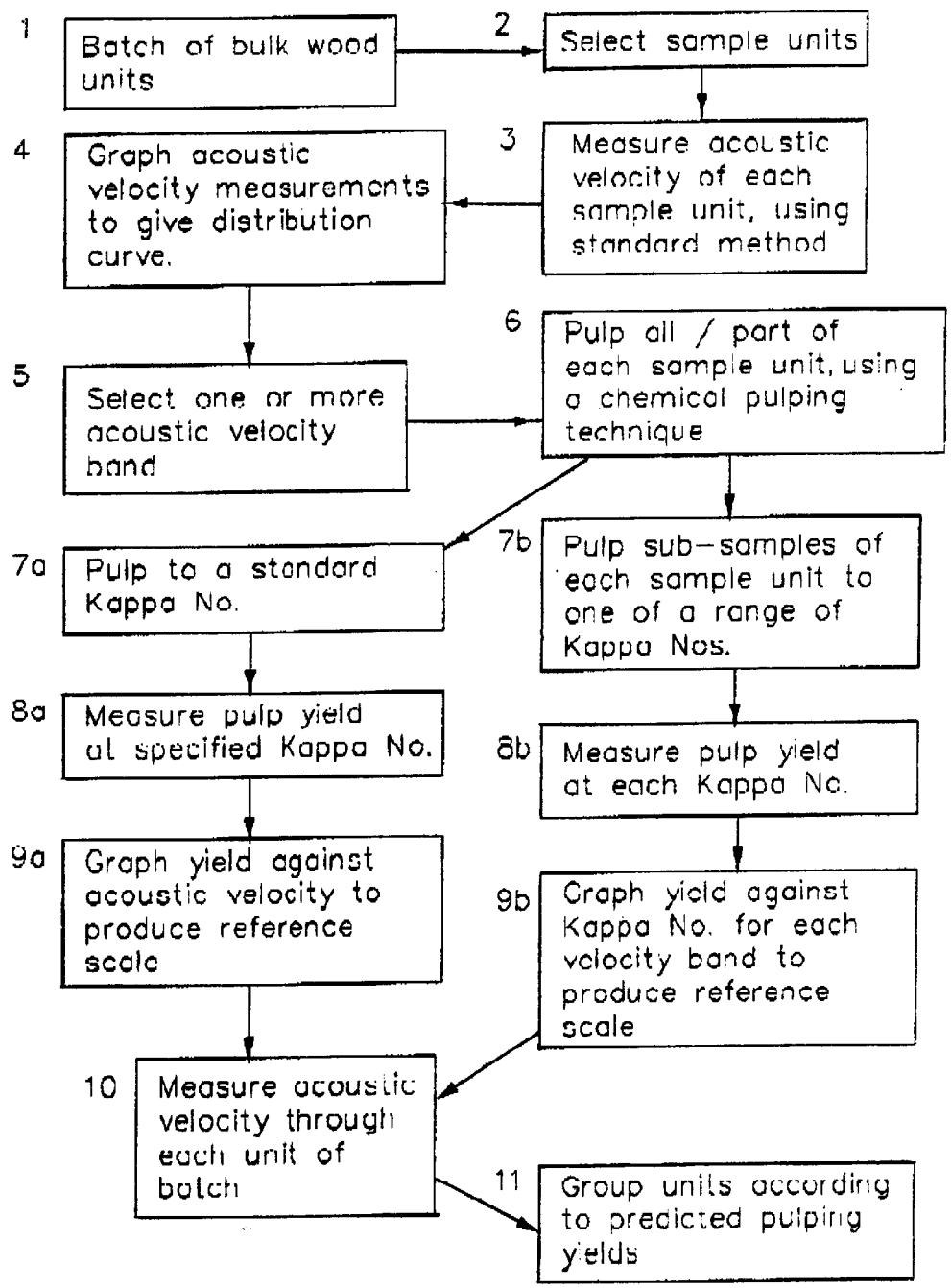
FIG. 1 is a flow chart illustrating the method of the present invention.

FIG. 1 illustrates the sequence of steps of utilising the present invention.

In step 1, each of the batch of bulk wood units is of the same or a similar species, and preferably also has a similar history, as defined above. Whilst it may be possible to treat all bulk wood units of the same tree species as forming part of the single batch i.e. being sufficiently similar to be classified using only a single set of reference tests, it is probable that before bulk wood units can be treated as forming part of a single batch, they must have a similar history. Thus, it is envisaged that separate reference tests will be required for bulk wood units of the same tree species but with a different history.

The extent to which separate reference tests are required will become apparent in the course of industrial use of the method of the present invention; as data are accumulated from large-scale use, it will become apparent to users of the method whether more or fewer reference tests are required to meet particular conditions.

In step 2, sample bulk wood units are selected from the batch, to carry out the detailed testing needed to establish a reference scale. Typically, 100–300 samples would be taken from a batch, assuming that the characteristics of the batch were completely unknown.

Figure 2:
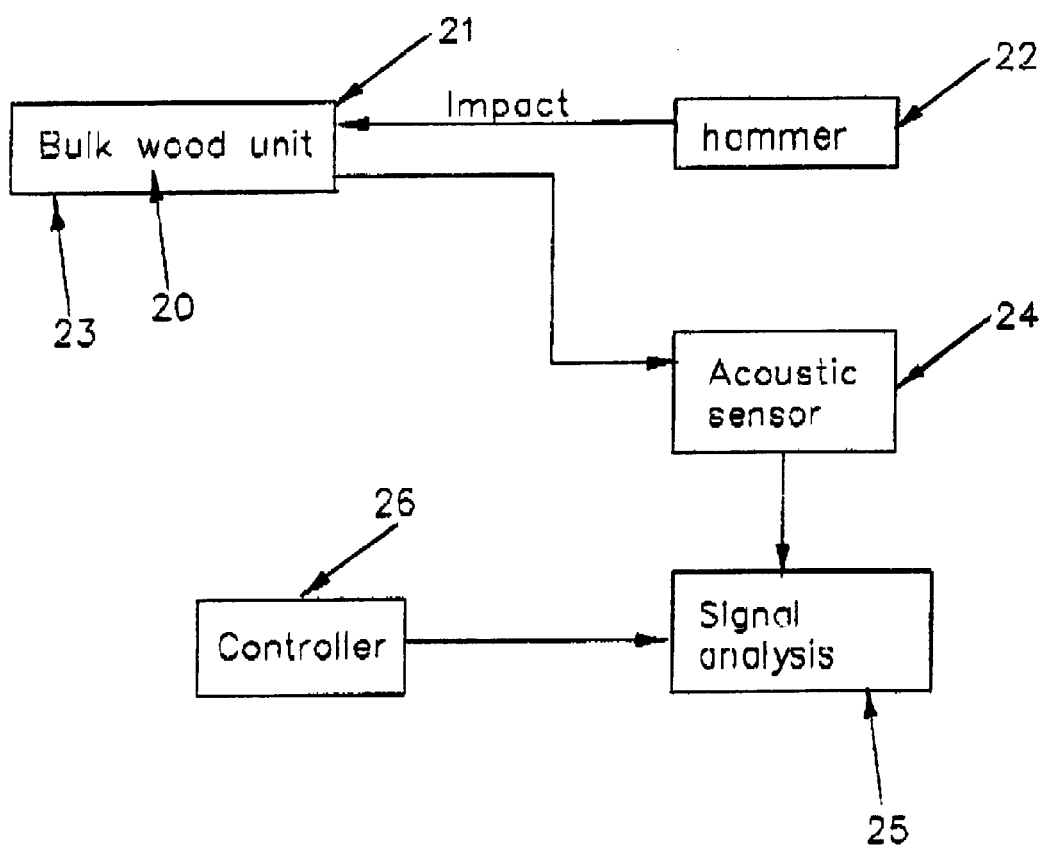
FIG. 2 is a diagram showing of the method of taking an acoustical measurement from a log.

In step 3, the acoustic velocity of each sample unit is measured, using the standard method represented diagrammatically in FIG. 2. The equipment for, and techniques for measurement of, acoustic velocity through a bulk wood units are known, and therefore are not described in detail. One typical system is shown in FIG. 2, in which a bulk wood unit 20 is supported and is struck on one end 21 by a hammer 22. The acoustic wave generated in the bulk wood unit by the impact of the hammer 22 travels down the length of the bulk wood unit, is reflected from the far end 23, and travels back to the end 21 where it is detected by an acoustic sensor 24. The detected signal is analysed by signal analysis apparatus 25, which also computes the velocity of the sound. The velocity is calculated from the time taken for the sound wave to travel along the length of a log and back divided by a distance equal to twice the length of a log. The apparatus is controlled by controller 26.

There are a number of known types of apparatus available for measuring acoustic velocity, and the above described equipment may be varied in a number of ways: for example, the velocity may be determined from a single reading taken at the opposite end of the bulk wood unit 21 to the hammer 22. Further, the hammer 22 may be replaced by any device capable of generating an acoustic wave in the bulk wood unit, e.g. a piezoelectric device or a wave from a sound generator.

Figure 3:
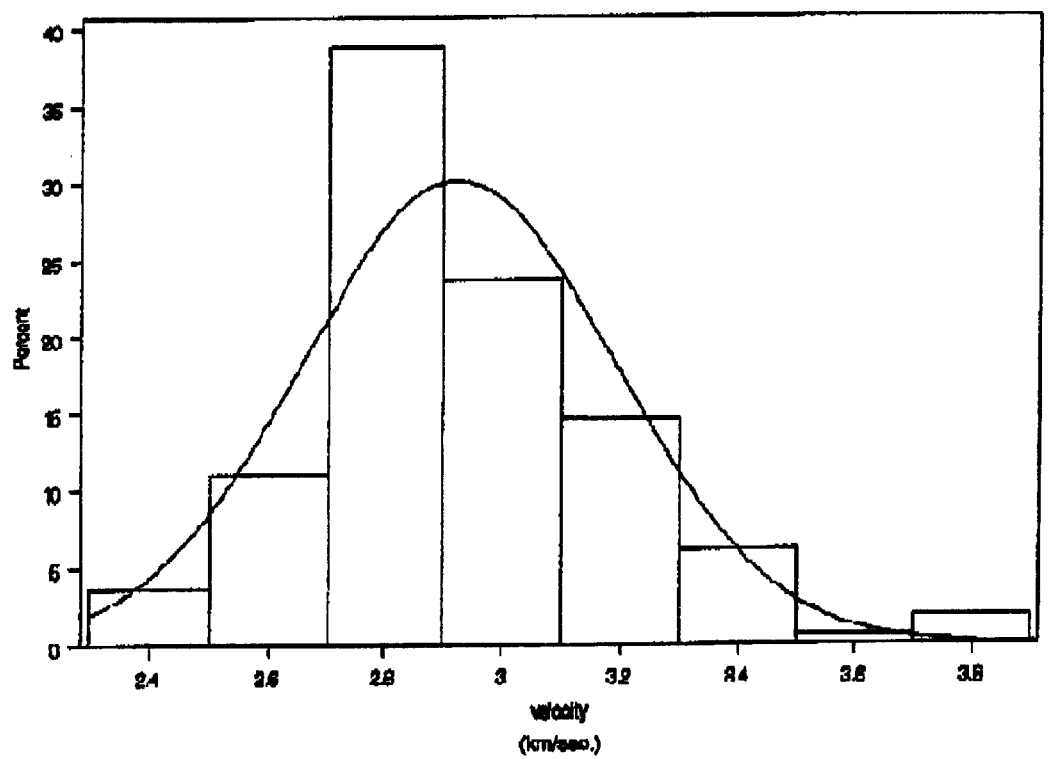
FIG. 3 is a distribution curve of the acoustic velocities in the sample units.

In step 4, the readings of acoustic velocity obtained in step 3 are graphed to give a distribution curve of the type shown in FIG. 3 which shows the distribution of acoustic velocities of a sample batch of 165 *pinus radiata* logs. The distribution curve shows the acoustic velocity range in which any specified percentage of the test samples fall. Thus, a study of the distribution curve enables the operator to select acoustic velocity bands which will include or exclude a specified percentage of the bulk wood units The actual figures selected for the acoustic velocity bands will depend upon the operator's requirements: if the operator wishes to select for chemical pulping only those bulk wood units which are optimum for this purpose, then only a single acoustic velocity may be selected, as discussed hereinafter.

It will be appreciated that the acoustic velocity bands may be used for grouping of the bulk wood units rather than for simply selecting or rejecting the units. As discussed above, it greatly increases the efficiency of chemical pulping if all of the units being pulped in a particular batch have a similar cellulose content. Thus, the acoustic velocity bands may be used to group together those bulk wood units predicted to have a similar cellulose content. The group or groups of bulk wood units which are predicted to have a relatively high lignin content would be more economically processed for unbleached paper, since the higher the lignin content in the pulp, the more bleaching the pulp requires.

It will be appreciated that the higher the efficiency of the chemical processing, the less effluent produced. Further, the higher the quality of the pulp produced (i.e. the higher its cellulose content) the less bleaching is required; this also reduces the bleach effluent.

Alternatively, the operator may wish to select acoustic velocity bands such that a majority of the bulk wood units would be selected for chemical pulping, and only those units which were clearly unsuitable would be rejected. In this case, the upper and lower limits of the acoustic velocity band into which the bulk wood units to be selected would fall, would be set to include a large proportion of the units e.g. a velocity $\geq 3.0$ km per second in the example shown in FIG. 3.

In step 6, all or a predetermined proportion of each sample bulk wood unit is pulped, using a standard chemical pulping technique such as the Kraft process.

Depending upon the requirements and practices of the particular pulpmill, the processing may be carried out using the route shown in steps 7a–9a, or the route shown in steps 7b–9b.

Figure 5:
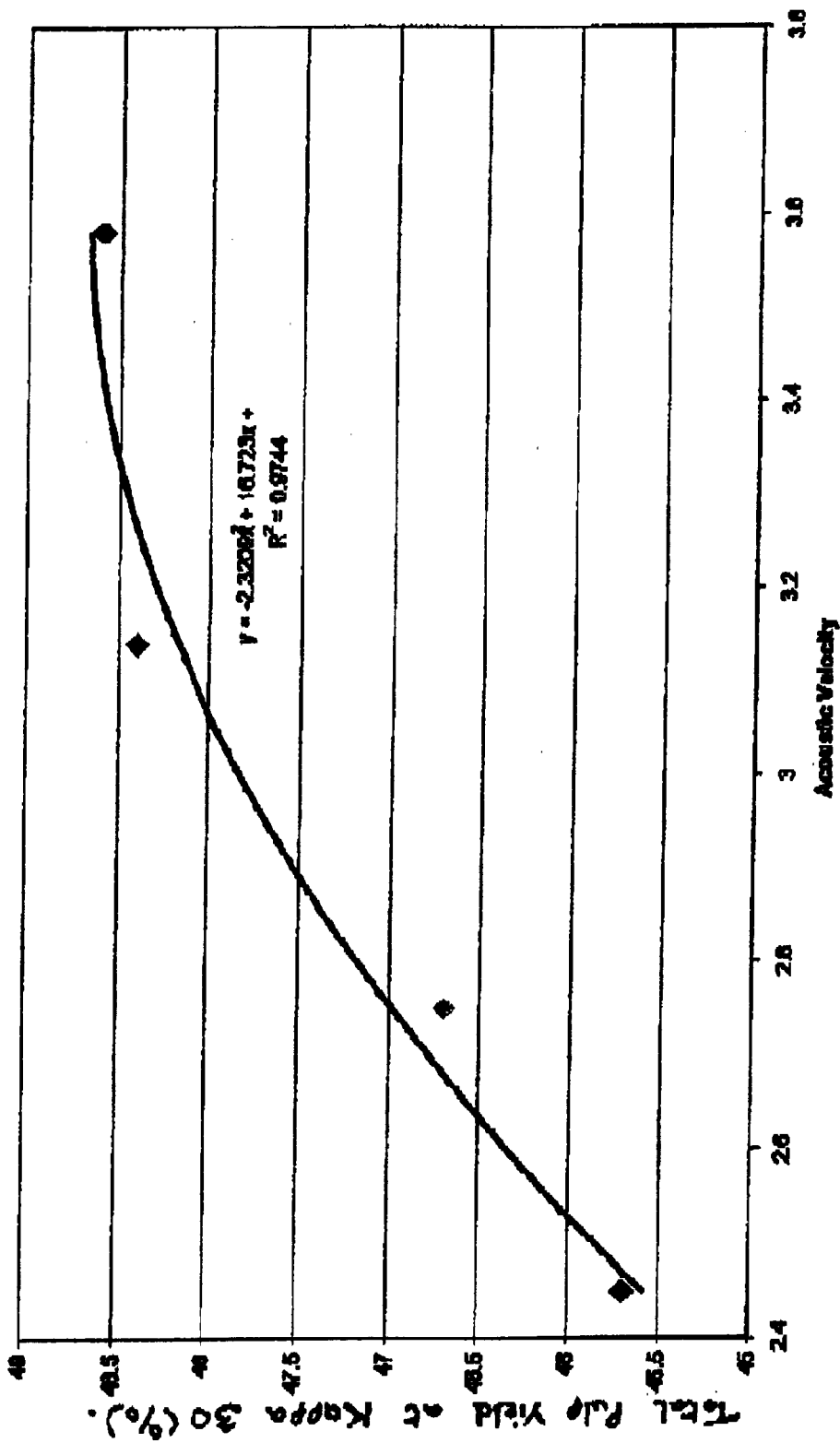
FIG. 5 is a graph of pulp yield versus acoustic velocity.

In the route shown in steps 7a–9a, the sample units are pulped to a standard Kappa number (typically in the range 20–30). This route would be used if the pulpmill requirements were for pulp only of a particular Kappa number. The pulp yield for each sample is then measured at the standard Kappa number, and a graph of pulp yield against acoustic velocity is prepared, giving a reference scale for that Kappa number. A typical graph is shown in FIG. 5, which shows the pulp yield at Kappa 30 against acoustic velocity, and clearly demonstrates the increase in pulp yield as the acoustic velocity increases. From a graph of this type, it is easy for an operator to select a suitable cut-off acoustic velocity for selecting bulk wood units for chemical pulping e.g. FIG. 5 shows that a suitable cut-off velocity would be 3 km per second.

In the alternative route shown in steps 7a–9b, a series of sub-samples from each pulp sample is processed, each to a different Kappa number. This route is used where the pulp mill requirements are somewhat more flexible, so that it is feasible to select a Kappa number which will optimise the yield.

Figure 4:
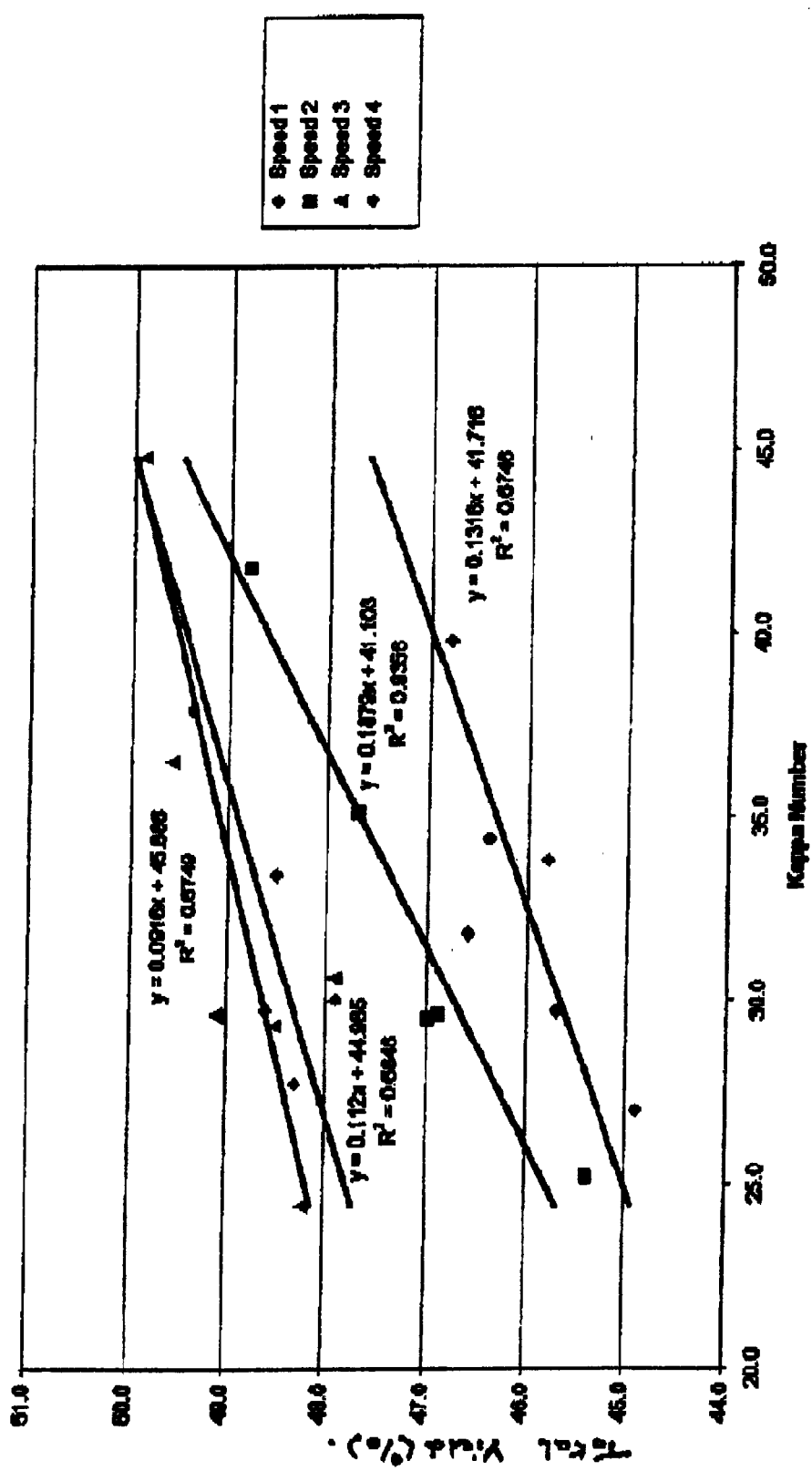
FIG. 4 is a graph of pulp yield versus Kappa number.

The pulp yield for each sub sample is measured, and a graph of yield against Kappa number for each velocity band is prepared, to produce a reference scale of the type shown in FIG. 4. A reference scale of this type can be used by an operator to select the optimum acoustic velocity band depending upon the intended processing conditions for that batch of bulk wood units.

In the typical results shown in FIG. 4, four velocity bands were selected:

Speed 1: velocity $\leq 2.52$ km/second.

Speed 2: velocity $\geq 2.7$ km per second but $\leq 2.8$ km per second.

Speed 3: velocity $\geq 3.1$ km per second but $\leq 3.2$ km per second.

Speed 4: velocity $\geq 3.4$ km per second.

The graph enables the operator to select the velocity band in which the desired level of pulp yield can be achieved for the required Kappa number (e.g. 30).

As FIG. 4 shows, the four velocity bands selected experimentally in practice group reasonably well into two separate bands, since the results for speed 1 and speed 2 lie close together, and the results for speed 3 and speed 4 also lie close together. It follows that for practical purposes, the results could be grouped into two acoustic bands for Kappa No. 30:

The first having a velocity <3 km per second;

The second having a velocity >3 km per second.

Of these first and second bands, the second gives a notably superior pulp yield at Kappa number 30. It follows that, in step 10, where the acoustic velocity through each unit of the batch of bulk wood units is measured, if those units are to be processed to Kappa number 30, then the operator should select for chemical pulping only those bulk wood units having an acoustic velocity greater than 3 km per second, since these are the units which will yield the highest percentage of pulp when processed to Kappa number 30.

The bulk wood units having an acoustic velocity less than 3 km per second could be diverted to other uses e.g. mechanical pulping, or could be used for chemical pulping in applications where the unbleached pulp is required.

However, if the bulk wood units are to be processed to a higher Kappa number e.g. a Kappa number 40 then the operator might decide to lower the acoustic velocity cut-off for selection to include the speed 2 group i.e. to select for chemical pulping bulk wood units which have an acoustic viscosity greater than 2.7 km per second, since the drop in pulp yield from the speed ¾ groups to the speed 2 group at this higher Kappa number is relatively small.

The reference scale of the type shown in FIG. 4 also may be reworked for any specified Kappa number to give a pulp yield/acoustic velocity graph of the type shown in FIG. 5.

In the steps described above, pulp yield is measured in the standard manner i.e. the percentage of dry pulp achieved from the dry matter of the bulk wood units.

What is claimed is:

1. A method for sorting a batch of bulk wood units from a timber group for chemical pulping in alkaline conditions, each of said bulk wood units having an acoustic velocity therethrough, said method comprising the steps of:

1) establishing a reference scale for the timber group to be sorted by:
    a) selecting at random a plurality of sample units or bulk wood from the timber group;
    b) measuring the acoustic velocity through each of said sample units using a predetermined measuring technique;
    c) recording said acoustic velocities and grouping said velocities into two or more velocity bands;
    d) processing all or part of each of said sample units to pulp using a predetermined chemical pulping process;
    e) determining the pulp yield from each sample;
    f) producing a reference scale indicating predicted pulp yield for a range of acoustic velocities;

2) measuring the acoustic velocity through each of said bulk wood units in turn, using said predetermined measuring technique;

3) comparing said acoustic velocity measurements against the reference scale to predict a chemical pulping yield for each tested unit; and 4) dividing said bulk wood units through which the acoustic velocity has been measured in step 2 into subgroups according to the chemical pulping yield predicted in step 3.

2. The method as claimed in claim 1 wherein before said acoustic velocity bands are selected, the acoustic velocities from all said sample units are graphed to show the distribution of acoustic velocity In the total sample, to enable the velocity bands to be selected such that a predetermined proportion of bulk wood units falls within each of the selected velocity bands.

3. The method as claimed in claim 2 wherein each of the batch of bulk wood units is of the same or similar species and has a similar history, in that each of the bulk wood units is of about the same age, has been grown under similar conditions, and managed in a similar fashion.

4. The method as claimed in any one of claims 1–3 wherein said reference scale comprises a graph of pulp yield against acoustic velocity for pulp processed to a specified Kappa number.

5. The method so claimed in any one of claims 1–3 wherein said reference scale comprises a graph of pulp yield against Kappa number for each of a series of acoustic velocity bands.

6. The method as claimed in claim 1 wherein said predetermined chemical pulping process is the Kraft process.

* * * * *

UNITED STATES PATENT AND TRADEMARK OFFICE
CERTIFICATE OF CORRECTION

PATENT NO. : 6,822,183 B2
DATED : November 23, 2004
INVENTOR(S) : John Corrie Fleming Walker It is certified that error appears in the above-identified patent and that said Letters Patent is hereby corrected as shown below:

Column 6,
Line 17, after "units", please delete "or" insert -- of --.
Line 57, after "method", please delete "so" insert -- as --.

Signed and Sealed this

Twenty-ninth Day of March, 2005

JON W. DUDAS
*Director of the United States Patent and Trademark Office*